United States Patent
Pedersen et al.

(10) Patent No.: US 10,328,210 B2
(45) Date of Patent: Jun. 25, 2019

(54) NON-AXIAL WORKING END-OF CONTENT MECHANISM AND AN INJECTION DEVICE COMPRISING THE SAME

(71) Applicant: Novo Nordisk A/S, Bagsvaerd (DK)

(72) Inventors: Simon Munch Pedersen, Copenhagen N (DK); Carsten Soerensen, Frederiksberg (DK); Simon Roervig, Copenhagen OE (DK)

(73) Assignee: Novo Nordisk A/S, Bagsvaerd (DK)

( * ) Notice: Subject to any disclaimer, the term of this patent is extended or adjusted under 35 U.S.C. 154(b) by 663 days.

(21) Appl. No.: 14/764,839

(22) PCT Filed: Jan. 31, 2014

(86) PCT No.: PCT/EP2014/000259
§ 371 (c)(1),
(2) Date: Jul. 30, 2015

(87) PCT Pub. No.: WO2014/117944
PCT Pub. Date: Aug. 7, 2014

(65) Prior Publication Data
US 2015/0367078 A1 Dec. 24, 2015

Related U.S. Application Data

(60) Provisional application No. 61/761,982, filed on Feb. 7, 2013.

(30) Foreign Application Priority Data

Feb. 1, 2013 (EP) ..................................... 13153628

(51) Int. Cl.
*A61M 5/315* (2006.01)
*A61M 5/20* (2006.01)

(52) U.S. Cl.
CPC .......... *A61M 5/31541* (2013.01); *A61M 5/20* (2013.01); *A61M 5/31553* (2013.01); *A61M 5/31558* (2013.01); *Y10T 74/20654* (2015.01)

(58) Field of Classification Search
CPC ................ A61M 5/31541; A61M 5/20; A61M 5/31553; A61M 5/31558; Y10T 74/20654
See application file for complete search history.

(56) References Cited

U.S. PATENT DOCUMENTS 2,991,662 A * 7/1961 Werner .................... G05G 5/04
475/14
3,411,366 A * 11/1968 Leto ......................... G05G 5/04
74/10.2

(Continued)

FOREIGN PATENT DOCUMENTS

CH            703993 A2    3/2012
CH            706567 A2    11/2013
(Continued)

OTHER PUBLICATIONS

European Patent Application 13153628.6, filed Feb. 1, 2013 by Novo Nordisk A/S.
(Continued)

*Primary Examiner* — Jenna Zhang
(74) *Attorney, Agent, or Firm* — Wesley Nicolas

(57) ABSTRACT

The invention relates to a non-axial working End-of-Content mechanism which is geared by a hypocycloid gearing. The EoC mechanism comprises a first element (30, 109) having a first internal surface (36, 136) with a first internal diameter (D), and an EoC element (50, 150) having a second external surface (56, 156) with a second external diameter (d) being smaller that the first internal diameter (D). The EoC element (50, 150) is located inside the first internal diameter (D) of the first element (30, 109) and the first element (30, 109) and the EoC element rotates relatively to each other in a gearing (Continued)

ratio. The EoC element (150, 150) thus operating as the inner rolling circle of a hypocycloid counting the numbers of relative rotations. The EoC mechanism further has stopping means (45, 55; 113, 155)) provided for stopping the relative rotation in a predetermined position which position correlates to the initial injectable content of drug in the injection device such that a user cannot at any time set a dose larger than the quantum left in the injection device at any time.

2 Claims, 6 Drawing Sheets

(56) References Cited

U.S. PATENT DOCUMENTS

| | | | |
|---|---|---|---|
| 4,973,318 A | | 11/1990 | Holm et al. |
| 5,104,380 A | | 4/1992 | Holman et al. |
| 5,114,406 A | * | 5/1992 | Gabriel ............... A61M 5/2033 604/134 |
| 5,263,475 A | * | 11/1993 | Altermatt ......... A61M 15/0065 128/203.15 |
| 5,279,585 A | | 1/1994 | Balkwill |
| 5,480,387 A | * | 1/1996 | Gabriel ................. A61M 5/20 604/134 |
| 6,582,404 B1 | * | 6/2003 | Klitgaard ........... A61M 5/31511 604/181 |
| RE41,956 E | | 11/2010 | Klitgaard et al. |
| 2004/0068236 A1 | * | 4/2004 | Moller .............. A61M 5/31525 604/208 |
| 2007/0225657 A1 | | 9/2007 | Hommann |
| 2008/0147005 A1 | * | 6/2008 | Moller ............. A61M 5/14566 604/134 |
| 2009/0275916 A1 | | 11/2009 | Harms et al. |
| 2010/0114025 A1 | * | 5/2010 | Moller ................. A61M 5/20 604/135 |
| 2012/0245532 A1 | | 9/2012 | Frantz et al. |
| 2014/0178233 A1 | * | 6/2014 | Shiotani ................ F04C 2/102 418/61.3 |
| 2015/0073355 A1 | * | 3/2015 | Hirschel .......... A61M 5/31541 604/189 |
| 2015/0265776 A1 | * | 9/2015 | Beek ..................... A61M 5/20 604/211 |
| 2016/0228651 A1 | * | 8/2016 | Plambech ............. A61M 5/20 |
| 2016/0235924 A1 | * | 8/2016 | Soerensen .............. A61M 5/24 |
| 2017/0224924 A1 | | 8/2017 | Christensen |

FOREIGN PATENT DOCUMENTS

| | | | |
|---|---|---|---|
| CN | 101060874 A | | 10/2007 |
| EP | 1861141 A1 | | 12/2007 |
| EP | 2814547 B1 | | 7/2015 |
| GB | 862641 A | | 3/1961 |
| WO | 9938554 A1 | | 8/1999 |
| WO | 200119434 A1 | | 3/2001 |
| WO | 2004/078226 | | 9/2004 |
| WO | 2006/058883 A2 | | 6/2006 |
| WO | 2006076921 A1 | | 7/2006 |
| WO | 2006086983 A1 | | 8/2006 |
| WO | 2007/017052 A1 | | 2/2007 |
| WO | 2008083875 A1 | | 7/2008 |
| WO | 2009105910 A1 | | 9/2009 |
| WO | 2009132778 A1 | | 11/2009 |
| WO | 2009150028 A1 | | 12/2009 |
| WO | 2011/039207 A1 | | 4/2011 |
| WO | 2011/068531 A1 | | 6/2011 |
| WO | 2013170392 A1 | | 11/2013 |
| WO | WO-2013170392 A1 * | 11/2013 | ........ A61M 5/31541 |
| WO | WO 2013170392 A1 * | 11/2013 | ........ A61M 5/31541 |
| WO | 2014/117944 A1 | | 8/2014 |
| WO | 2016/016184 A1 | | 2/2016 |

OTHER PUBLICATIONS

U.S. Appl. No. 61/761,982, filed Feb. 7, 2013 by Nova Nordisk A/S.

* cited by examiner

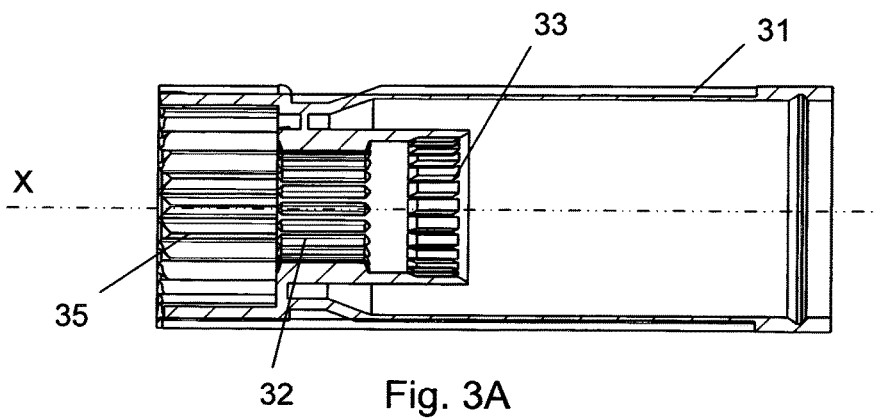
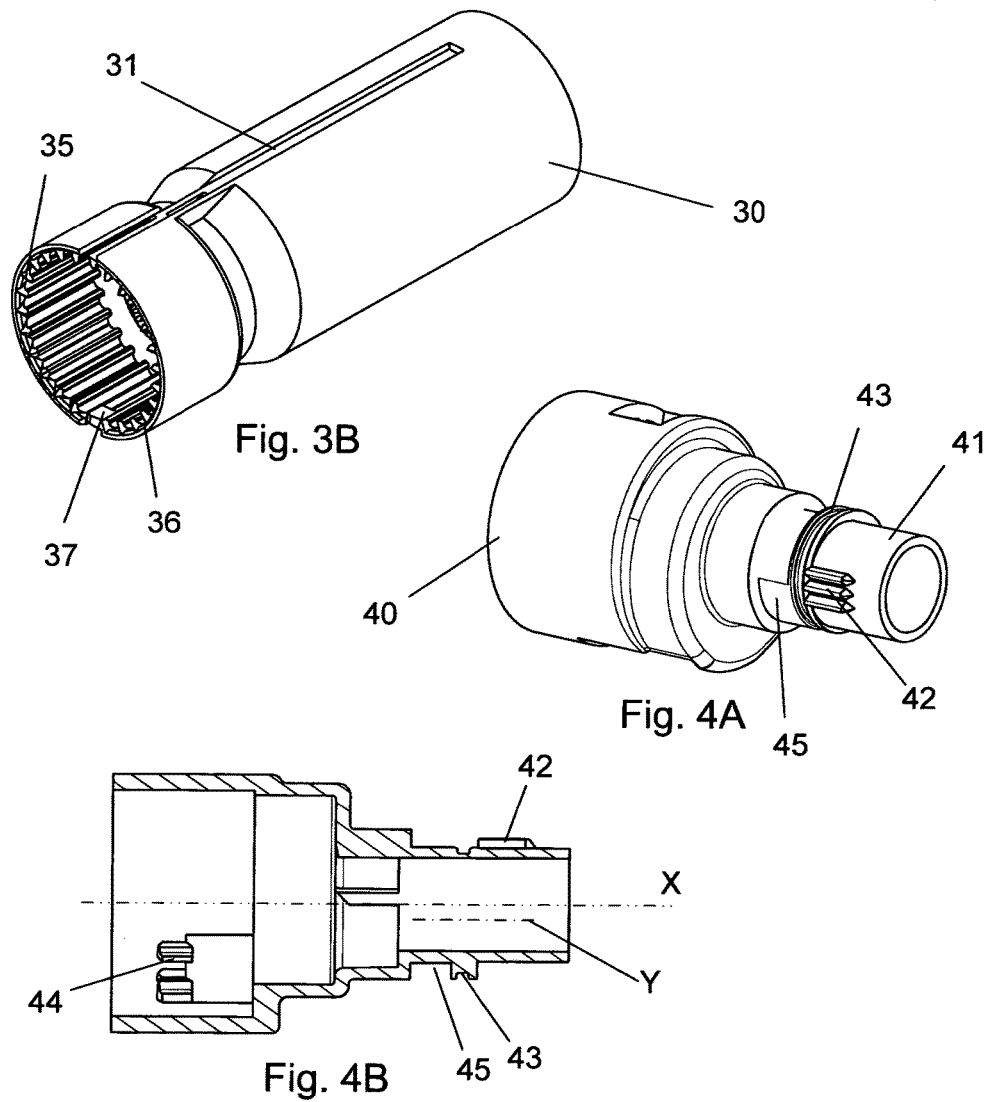

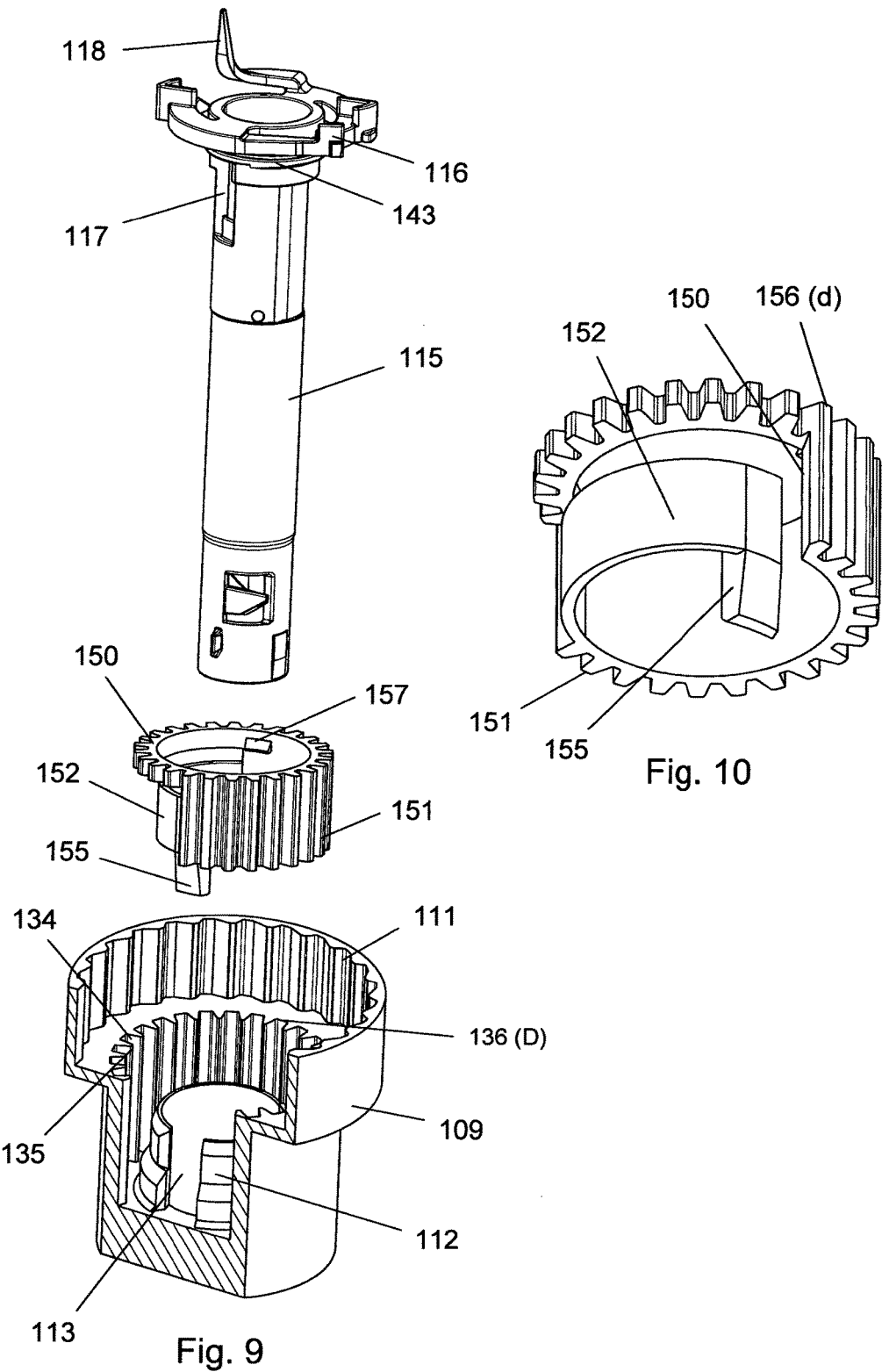

NON-AXIAL WORKING END-OF CONTENT MECHANISM AND AN INJECTION DEVICE COMPRISING THE SAME

CROSS-REFERENCE TO RELATED APPLICATIONS

This application is a 35 U.S.C. § 371 National Stage application of International Application PCT/EP2014/000259 (published as WO 2014/117944), filed Jan. 31, 2014, which claims priority to European Patent Application 13153628.6, filed Feb. 1, 2013; this application claims priority under 35 U.S.C. § 119 to U.S. Provisional Application 61/761,982; filed Feb. 7, 2013.

THE TECHNICAL FIELD OF THE INVENTION

The invention relates to an End-of-Content for an injection device. The invention specifically relates to such End-of-Content mechanism which operates without any axial movement thus making it suitable to be built into relatively short injection devices and especially to an EoC mechanism based on a hypocycloid gearing.

DESCRIPTION OF RELATED ART

Injection devices for injecting an adjustable amount of a liquid drug usually have a button that a user rotates to set the adjustable size of the dose to be injected. Such injection devices holds a cartridge containing a specific amount of liquid drug and is usually equipped with a mechanism which secures that a user cannot set a dose size which exceeds the injectable amount remaining in cartridge at any time.

In mechanical injection devices this mechanism is usually some kind of counter which is moved whenever a dose is set but maintained in its new position when the dose is injected. The position of the counter is thus an expression of the accumulated doses set by the user. The movement of the counter is then restricted in accordance with the initial quantum in the cartridge such that the counter is blocked in its movement when the accumulated doses set equals the initial injectable quantum in the cartridge.

Such mechanism is often referred to as an End-of-Content (EoC) mechanism and a very simple example is provided in U.S. Pat. No. 4,973,318. In this injection device the counter nut is formed integral with the dose setting button and is rotated up the threaded piston rod when a dose is set. When the set dose is injected, the counter nut is maintained in its relatively position on the thread of the piston rod as the dose setting button and the piston rod is moved axially forward. The length of the thread correlates to the initial quantum of liquid drug in the cartridge and once the counter nut reaches the end of the thread no further dose can be set.

However, in this injection device the axial distance the injection button is moved during injection corresponds to the axial distance that the piston rod is moved forward inside the cartridge.

More modern injection devices has a gearing mechanism such that the piston rod can be moved a different length than the injection button is moved. An End-of-Content mechanism for such modern injection devices is disclosed in U.S. Pat. No. RE41,956.

FIG. 3 of U.S. Pat. No. RE41,956 discloses an embodiment in which a counter nut is moved up a helical track on a driver whenever a dose setting member is rotated. During injection, the counter nut is maintained in its relative position in the helical track such that the position of the counter nut in the helical track at any time is an expression of the accumulated doses set by the user. The length of the helical track correlates to the initial quantum of liquid drug in the cartridge and once the counter nut reaches the end of the helical track, the dose setting member cannot be rotated further thus a dose larger than what corresponds to the length of the helical track cannot be set.

FIG. 2 of U.S. Pat. No. RE41,956 discloses a different embodiment wherein the End-of-Content mechanism is non-axial working. Here the driver is provided with a spiral track and the dose setting member is provided with a track follower engaging the track. The track and the track follower is rotated relatively to each other during dose setting but maintained in a relatively fixed position during injection. Once the spiral track ends, the track follower and thus the dose setting member cannot be moved further. However, since the length of the spiral track has to correlate to the initial quantum of drug in the cartridge, the driver need to have a rather large diameter which disqualifies the use of this type of EoC mechanism in pen shaped injection devices.

A different End-of-Content mechanism is disclosed in EP 1,861,141. In this EoC mechanism a first rotatable element rotates a second rotatable element one increment for each full rotation of the first element. A mechanism is provided which moves the second element axially in relation to the first element such that the two elements only engages and rotate together once for each full rotation of the first element. Once the second element has been rotated a specific and predetermined number of times the second element is arrested by a stop means and thus prevents both the second element and the first element from being rotated further. However, the axial movement of the second rotatable element requires axial space inside the injection device.

In the recent years automatic spring driven injection devices have become very popular. These injection devices has a spring, often a torsion spring, which is strained during dose setting and released to drive a piston rod forward during injection. Since the spring provides the force to drive the injection there is no need for the user to push an injection button back into the housing of the injection device during injection. These new injection devices therefore have no part which grows out from the housing during dose setting in order for a user to push the same part back into the housing during dose injection. As a result these automatic injection device has the same length all the time.

An example of an End-of-Dose mechanism for such automatic injection device is disclosed in WO2007/017052. Here a counter nut is screwed up the thread on the threaded piston rod when a dose is set and maintained in its relative position during dose injection. Once the counter nut reaches the end of the thread on the piston rod, the counter nut prevents the dose setting member from being rotated any further thereby preventing a further dose in being set. The length of the thread on the piston rod correlates to the initial amount of liquid drug in the cartridge such that the counter nut reaches the end of the track when the initial quantum has been repetitive set.

A drawback for all these known End-of-Content mechanism is that they require either a substantial axial length of the injection device due to the axial working element or a relatively large diameter in order to carry the spiral track as in U.S. Pat. No. RE41,956 FIG. 2.

DESCRIPTION OF THE INVENTION

It is an object of the present invention to provide an injection device in which the End-of-Content mechanism has no axial working component and which can be fitted into a pen shaped injection device having a short length and a limited diameter.

The invention is defined in claim 1. Accordingly in one aspect the present invention relates to a mechanical counter mechanism which requires no axial movement for counting.

The EoC mechanism basically comprises;
A first element having a first internal surface defining an internal diameter (D), and
An EoC element (or second element) having an external surface defining an external diameter (d).
The external diameter (d) of the EoC element is smaller than the internal diameter (D) of the first element and the EoC element is located inside the first diameter (D) of the first element.

The first element has a first centre axis (X) and the EoC element has a second centre axis (Y) which is dislocated in relation to the first centre axis (X) such that the external surface of the EoC element abuts and rolls on the internal surface of the first element. The EoC element thus operates as the inner rolling circle of a hypocycloid and rotates relatively to the first element in a gearing ratio.

Further, stopping means are provided for stopping the relative rotation of the first element and the EoC element in a predetermined position. The relative rotation is thus stopped when the EoC element enters into a predetermined position relatively to the first element. Whenever the first element and the EoC element rotate relative to each other a fixed point on the EoC element is rotated a certain angle on the internal surface of the first element. Once the accumulated angular movement of this fixed point correlates to the initial quantum of liquid drug in the injection device a stop is provided which prevents the EoC element from further rotation.

The stop or stopping means are provided for stopping the rotation of the EoC element in a predetermined position, which predetermined position correlates to the initial injectable quantum of liquid drug in the cartridge. The stopping means in this way stops the EoC element from rotating further when the EoC mechanism and especially the dose setting button which is coupled to the rotational part of the EoC mechanism has been rotated through a predefined number of rotations. The predetermined number of rotations relate to the initial content of liquid drug in the injection device such that the EoC element keep track of the accumulated doses set (and expelled) and stops the EoC element in a predetermined position where the injection device runs dry from liquid drug. By using such EoC mechanism it is not possible at any time to set a dose larger than the quantum of liquid drug remaining in the injection device.

A preferred way of obtaining a dislocated centre line (Y) of the EoC element is to mount the EoC element rotational on an eccentric cam provided on a third element which operates as an axis for the EoC element.

In a first embodiment, this third element is kept inrotatable during setting and the first element is rotated during dose setting e.g. by being rotational coupled to the dose setting button. This coupling between the dose setting button and the first element is preferably designed such that the first element rotate whenever the dose setting button is rotated, but not necessarily in the same ratio. The dose setting button is usually rotatable in both directions such that the set dose size can be adjusted by rotation in a direction opposite of the dose dialing direction.

In this embodiment the EoC element rotates in the same rotational direction as the first element and rotate a greater angle than the first element is rotated thus when the first element is rotated one full revolution, the EoC element has rotated more than one full revolution. The relative position of the EoC element within the first element is at all times an expression of the accumulated number of set doses. In each operation of the injection device, the set doses are also expelled such that each new setting commence with the scale drum in its zero position.

In a second embodiment the third element is rotated to set a dose and the first element is kept inrotatable during dose setting. The third element is in this embodiment preferably coupled to the dose setting button to follow the rotation of the dose setting button e.g. in a ratio.

The result being that the EoC element rotates in a rotational direction opposite to the rotation of the third element. The EoC element thus rotates a smaller angle than the third element. However, also for this embodiment a fixed point on the EoC element is angular moved in relation to the first element and the accumulated angular movement of the fixed point on the EoC element is an expression of the accumulated set and expelled doses.

Decisive for the angular difference (angular ratio) in rotation between the two elements in the hypocycloid is the ratio between the circumferences (which is also the diameter or radius ratio) of the two elements as will be explained in details later.

This EoC mechanism has a very limited diameter and has no components operating in the axial direction when counting. It is therefore very suitable as an alternative to the known End-of-Contents mechanisms and especially suitable to be built into short injection devices having a limited diameter.

The fact that the EoC mechanism does not move axially during counting does not hinder that elements of the injection device are shifted in an axial direction e.g. when moving from a dose setting mode to an injection mode. The element so moved axially could be one or more of the elements carrying parts of the EoC mechanism. However, during counting the elements of the EoC mechanism is maintained in the same axial position, which is also a major benefit of the invention.

When shifting from the dose setting mode in which the counter counts to the dose injection mode in which the counter remains in its relative position, parts of the EoC mechanism, including the EoC element, can be slided axially. This axial movement of parts of the EoC mechanism does not influence the counting ability of the EoC mechanism, but is purely a movement made during injection of the set dose.

When the EoC mechanism is integrated in an automatic torsion spring driven injection device e.g. of the type described in International patent application No. PCT/EP2013/071451, the axial movement of the first part and of the EoC element done during injection could arise from an axial movement of a needle shield. This is usually referred to as shield release. However, the axial movement could also arise from axial movement of an injection button.

The axial movement during injection is however very limited. The axial movement is reduced to only the movement needed to move the clutch parts in and out of engagement in order to release the torque of the torsion spring.

The two different operational modes are defined as follows.

In the dose setting mode, the first element and the EoC element rotate relatively to each other thus counting and accumulating the size of the set doses.

In the first embodiment, the first element is rotated which again causes the EoC element to rotate. In the second embodiment, the third element is rotated thus causing the EoC element to rotate.

In the dose injection mode, the first element and the EoC element remain in their respective relative rotational position i.e. no counting occurs.

The first element and the EoC element preferably engage each other via a toothed interface. The first element has teeth separated by valleys provided on its internal surface engaging similar teeth on the outside surface of the EoC element. Such toothed engagement improves the rotation of the EoC element by the rotation of the first element.

In the example provided the toothed interface is established such that the ratio between the teeth on the first element and on the EoC element equals, or at least approaches, the angular ratio. With 26 teeth on the first element and 25 teeth on the EoC element, the ratio between the teeth is 1.04 and a specific tooth on the EoC element is thus brought one valley on the first element forward or backwards for each full rotation as will be explained later.

Two examples are provided in this application; In the first example, the first element is the rotating element coupled to the dose setting button and the EoC element rotates an angel of more than 360 degrees in the same direction (as the first element) whenever the first element is rotated 360 degrees. The toothing is preferably calculated such that a specific tooth on the EoC element is brought forward one increment for each full rotation of the first element. Here one increment equals a stepwise movement into the next consecutive valley on the first element.

In the second example, the third element is the rotating element coupled to the dose setting button and the EoC element rotate in the opposite direction (of the third element). The EoC element is thereby brought a smaller angle in the opposite direction every time the third element is rotated 360 degrees in a first direction. The toothing is preferably calculated such that this smaller angle results in a specific tooth on the EoC element rotate one increment for each full rotation of the third element. Also in the second example, one increment equals a stepwise movement into the next consecutive valley on the first element.

However a discrepancy in the angular ratio and the ratio in the numbers of teeth can result in the need for additional teeth as will be explained later.

Further the stopping means are operational between the first element and the EoC element. These stopping means preferably include a flexible arm coupled to the EoC element e.g. moulded as an integrated part of the EoC element. When reaching the stopping position this flexible arm can be moved radially such that a hook provided on the flexible arm, engages a cut-out which is preferably provided on the third element. As the third element is inrotatable, at least in the dose setting mode, relative rotation between the EoC element and the first element are prevented.

In the first embodiment, the flexible arm are preferably lifted radially inward when a single tooth provided on the flexible arm encounters an obstacle provided on the internal surface of the first element. This obstacle could e.g. be a filled-out valley between two subsequent teeth. The valley needs only be partly filled out as only the specific area encountered by the single tooth of the flexible arm needs to be filled out in order to lift the flexible arm inwardly. The EoC mechanism is thus prevented from further rotation when the flexible arm is raised and the hook engages the cut-out in the third element.

In the second embodiment, the flexible arm abuts a surface of a tower which is preferably a part of the first element. The flexible arm has an inherent resiliency and is guided against this surface with a certain tension. The surface is provided with an opening into which the hook on the flexible arm will drop when the EoC element reaches its end position. In this position, the EoC element will be rotational locked to the first element.

In a second aspect the invention relates to a torsion spring driven injection device as described in International patent application No. PCT/EP2013/071451 in combination with the EoC mechanism described herein.

In such injection device, according to the first embodiment, the third element carrying the EoC element is preferably moved in the axial direction to release the torque of the torsion spring by an axial movement of a needle shield covering the injection needle between injections. During the axial movement of the third element, the EoC element also slides axially.

According to the second embodiment, the third element carrying the EoC element is also moved axially together with the EoC element during injection.

DEFINITIONS

An "injection pen" is typically an injection apparatus having an oblong or elongated shape somewhat like a fountain pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"I.U" or "International Units" is a unit of measurement for the amount of a substance based on the biological activity of the substance. 1 I.U. of e.g. insulin therefore defines a specific mass of the active insulin type. For human insulin international standards define that 26 IU of insulin is equivalent to 1 milligram of dry, crystalline insulin. The strength of liquid insulin is usually expressed as a number of I.U per milliliter e.g. 100 IU/ml or 200 IU/ml, often simply expressed as an U100 or an U200 insulin. However, any number of I.U can be applied to any given volume.

"Scale drum" is meant to be a cylinder shaped element carrying indicia indicating the size of the selected dose to the user of the injection pen. The cylinder shaped element making up the scale drum can be either solid or hollow. "Indicia" is meant to incorporate any kind of printing or otherwise provided symbols e.g. engraved or adhered symbols. These symbols are preferably, but not exclusively, Arabian numbers from "0" to "9". In a traditional injection pen configuration the indicia is viewable through a window provided in the housing.

"Cartridge" is the term used to describe the container containing the drug. Cartridges are usually made from glass but could also be moulded from any suitable polymer. A cartridge or ampoule is preferably sealed at one end by a pierceable membrane referred to as the "septum" which can be pierced e.g. by the back-end of a needle cannula. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Since a cartridge usually has a narrower neck portion into which the rubber plunger cannot be moved, not all of the drug contained inside the cartridge can be expelled. The term "initial quantum" therefore refers to the initial quantum of the injectable content. The term "remaining content" in the same way refers to the remaining injectable content.

Further the term "injection needle" defines a piercing member adapted to penetrate the skin of a subject for the purpose of delivering or removing a liquid.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIG. 3A-B shows different views of the first element.

FIG. 4A-B shows different views of the third element.

FIG. 9 shows an exploded view of the hypocycloid EoC mechanism according to a second embodiment of the invention.

FIG. 10 shows a perspective view of the EoC element of the second embodiment.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device which usually carries the injection needle whereas the term "proximal end" is meant to refer to the opposite end pointing away from the injection needle and usually carrying the dose dial button.

FIGS. 1 to 8 discloses a first embodiment which will hereafter be explained in details.

Figure 1:
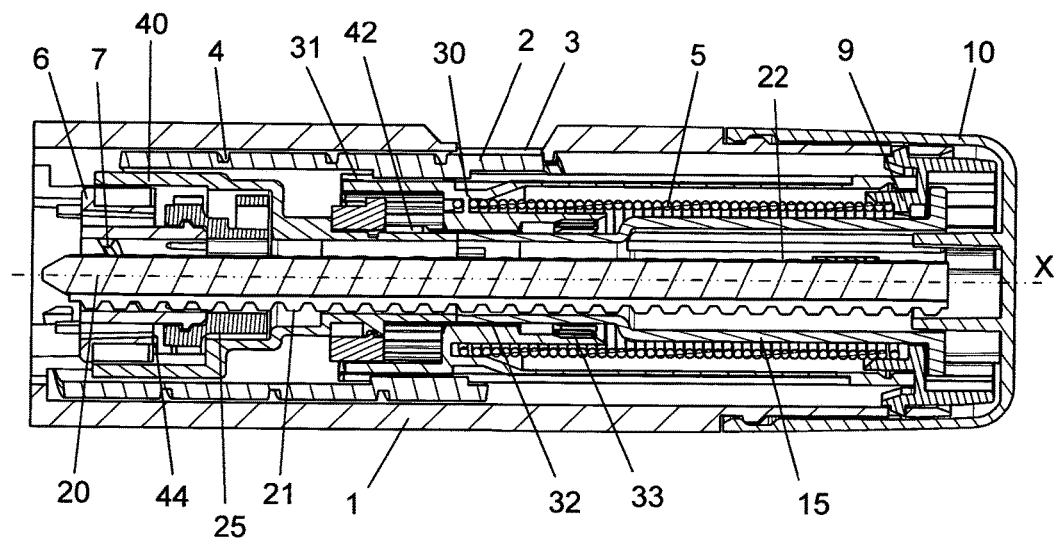
FIG. 1 shows a cross sectional view of the dose setting and injection mechanism of the injection pen according to International patent application No. PCT/EP2013/071451.

FIG. 1 discloses a torsion spring driven injection device according to International application No. PCT/EP2013/071451.

The basic elements of this injection device are:

A housing 1 encompassing the various components,

A scale drum 2, which visually informs the user of the dose size through a window 3 in the housing 1. The scale drum 2 is preferably threaded to the housing 1 via an external thread 4 and splined to the drive tube 30 via a longitudinal recess 31 in the drive tube 30 such that the scale drum 2 rotates with the drive tube 30 and performs a helical movement in relation to the housing 1.

A dose setting button 10 which is rotatable mounted to the housing 1 at a proximal end and by which button 10 the user can set and adjust the size of the dose to be injected.

A piston rod 20 for moving a plunger forward inside a cartridge containing the liquid drug to be injected. The piston rod 20 has a thread 21 on its outer surface and is further provided with a longitudinal extending track or similar not circular outer cross section 22.

The drive tube 30 is connected to a torsion spring 5 which proximally is secured to a spring base 9. The spring base 9 is inrotatable retained in the housing 1 such that the torsion spring 5 is strained when the drive tube 30 is rotated via the dose setting button 10.

Distally, the housing 1 is provided with a nut element 6. This nut element 6 is in the disclosed example moulded as an integral part of the housing 1, but could alternatively be provided as a separate part inrotatable retained in the housing 1. The nut element 6 has an internal thread 7 engaging the outer thread 21 of the piston rod 20. Further the nut element 6 rotatable supports a piston rod guide 25.

The piston rod guide 25 engages the longitudinal track 22 of the piston rod 20 such that rotation of the piston rod guide 25 is transferred to a rotation of the piston rod 20. Once the piston rod 20 is rotated it is screwed forward in the thread 7 of the nut element 6.

A clutch 40 slides on an outside surface of the nut element 6 as disclosed in FIG. 1 which discloses the injection device in the dose setting mode. In this mode the clutch 40 engages the nut element 6 via the internal teeth 44 (see also FIG. 4B) thus preventing the clutch 40 from rotating in the dose setting mode.

During injection the clutch 40 is axially moved in the proximal direction; out of engagement with the nut element 6 and into engagement with the drive tube 30 such that the torque in the torsion spring 5 rotates the drive tube 30, the clutch 40 and the piston rod guide 25 together which results in rotation of the piston rod 20 thus moving the piston rod 20 in the distal direction.

As the clutch 40 moves axially when shifting from the dose setting mode (FIG. 1) to the dose expelling mode, so does the EoC ring 50 as it follows the axial movement of the clutch 40. The teeth 35 on the internal surface 36 and the separating valleys 34 have a longitudinal length supporting this axial movement.

Figure 2:
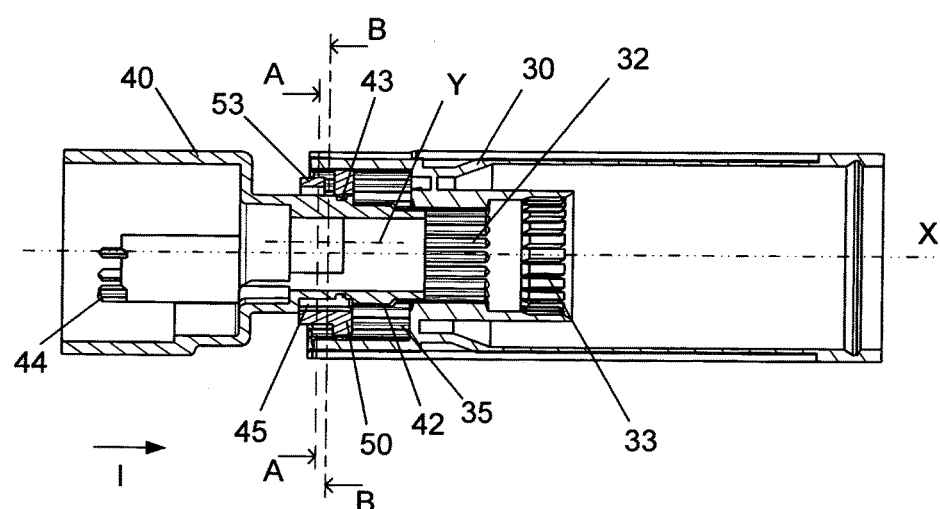
FIG. 2 shows a cross sectional view of the End-of-Content mechanism according to a first embodiment of the invention.

The non-axial working End-of-Content mechanism itself is further disclosed in FIG. 2 and consists of three parts; the drive tube 30, the clutch 40 and an EoC ring 50.

As in FIG. 1, FIG. 2 also discloses the dose setting mode. The clutch 40 is rotational locked to the nut element 6 and the drive tube 30 is able to rotate when the user rotates the dose setting button 4.

During injection, the clutch 40 is moved proximally (as indicated by the arrow "I" in FIG. 2) such that the teeth 42 engages the toothed ring 32 of the drive tube 30 whereby the clutch 40 rotate together with the drive tube 30. At the same time a second clutch element 15 is moved proximally out of engagement with the proximal toothed ring 32 of the drive tube 30 which releases the drive tube 30 to rotate under influence of the torque of the torsion spring 5.

In the second embodiment depictured in the FIGS. 9 to 12, the second clutch in numbered "115".

Figure 5A:
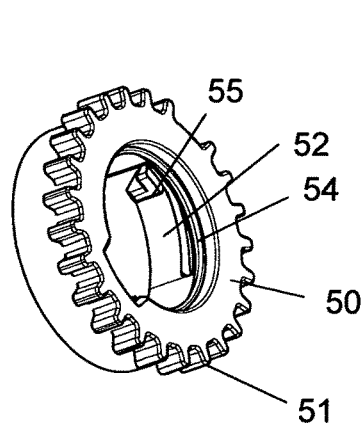
FIG. 5A-C shows different views of the EoC element.
Figure 5C:
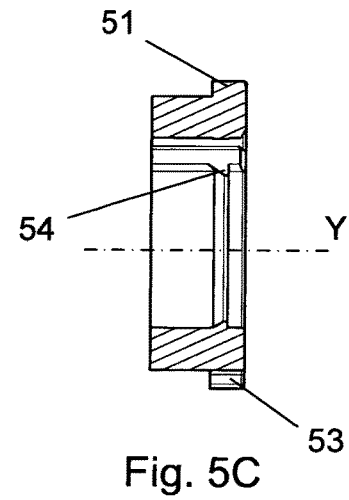
Figure 5B:
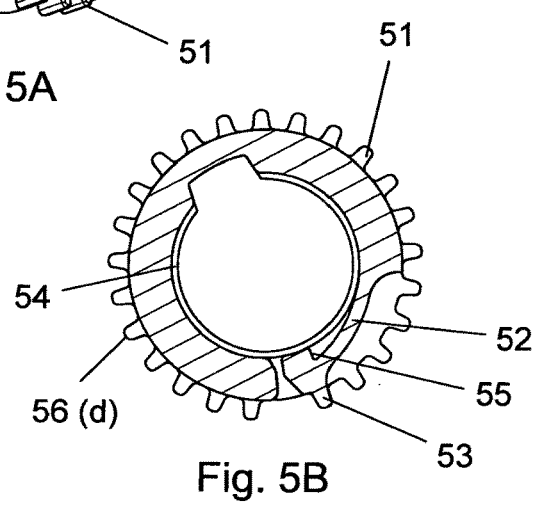

FIG. 3 discloses the drive tube 30, FIG. 4 discloses the clutch 40 and FIG. 5 discloses the EoC ring 50.

FIG. 3 discloses the drive tube 30. Distally the internal surface 36 has inwardly pointing teeth 35 separated by valleys 34 (see FIG. 7), however one such valley is filled out thus providing a double tooth 37.

The various engagement of the drive tube 30 is as follows;

The distally provided teeth 35 engage the teeth 51 on the EoC ring 50 in both the dose setting mode and in the dose injection mode.

The next ring of teeth 32 engages the teeth 42 on the clutch 40 when in the dose injection mode. In the dose setting mode no engagement is present but the internal teeth 44 on the clutch 40 engage with the nut element 6.

In the dose setting mode the proximal ring of teeth 32 engages similar teeth provided on the second clutch element 15. In the dose injection mode this engagement is released by proximal movement of the second clutch 15.

The further ring of teeth 33 is in contact with arms provided on the second clutch element 15 to produce a click-sound when the drive tube 30 rotate relative to the second clutch element 15, which it does during dose expelling.

The clutch 40 disclosed in FIG. 4 has a proximally extending tube 41 which carries teeth 42 and an eccentric cam 43. At its proximal end, the clutch 40 abuts the second clutch element 15. As shown in FIG. 2, the EoC ring 50 is carried on the cam 43. The eccentric outer surface of the cam 43 keeps the EoC ring 50 in contact with the internal surface 36 of the drive tube 30. The cam 43 has a centre line Y which is dislocated in relation to the centre axis X of the injection device. The centre line X is also the centre line for both the clutch 40 and the drive tube 30.

Distally to the cam 43 the clutch 40 is externally provided with a cut-out 45 which is to be engaged by the hook 55 of the EoC ring 50 as will be explained later.

Figure 6:
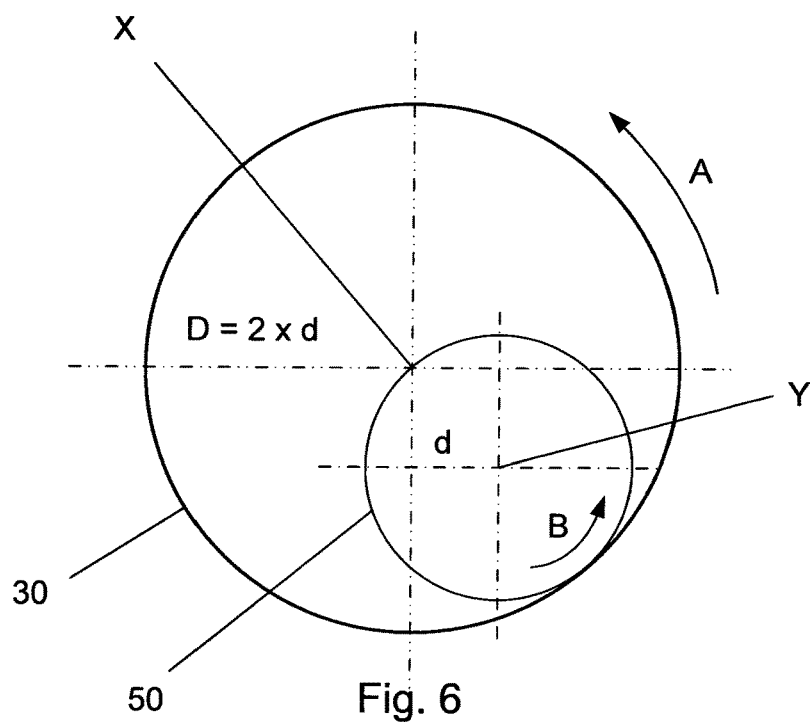
FIG. 6 shows the working principle of a hypocycloid gearing mechanism.

Further, the EoC ring 50 has an external surface 56 having an external diameter (d) which is smaller than the internal diameter (D) of the internal surface 36 of the drive tube 30 thus making the connection between the EoC ring 50 and the drive tube 30 operate as a hypocycloid gearing as schematically shown in FIG. 6.

The EoC ring 50 disclosed in FIG. 5 is proximally provided with a ring of external teeth 51 and distally provided with a flexible arm 52 carrying a single tooth 53.

Internally the EoC ring 50 has a circular rim 54 which engages the eccentric cam 43 of the clutch 40 such that the EoC ring 50 is able to rotate around the extending tube 41 with a centre line Y which is dislocated from the centre line X of the injection device.

Figure 7:
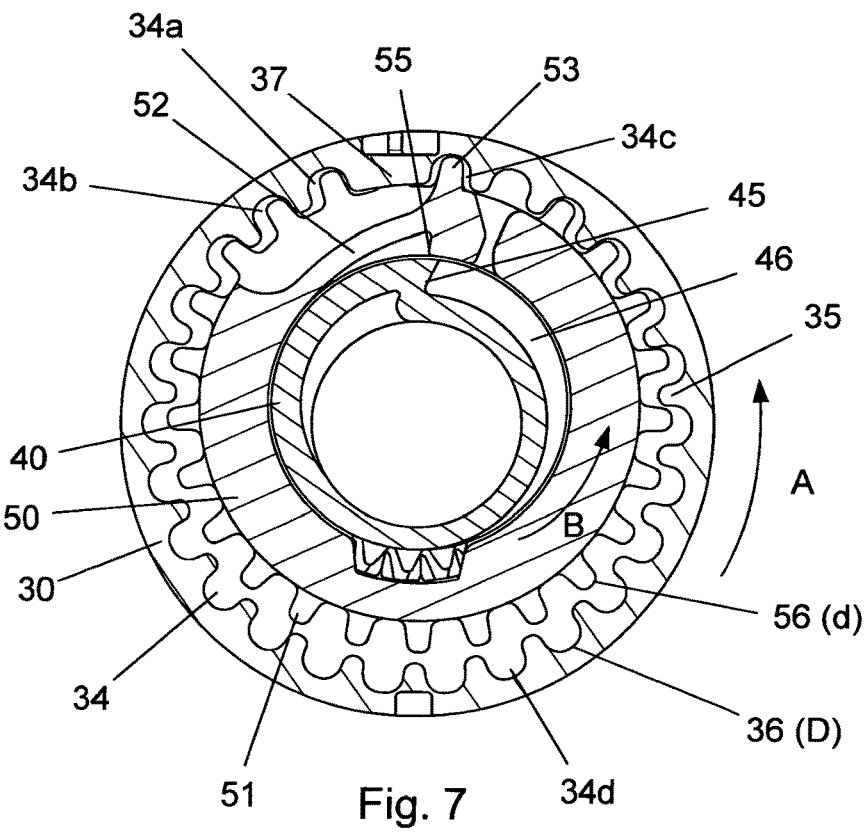
FIG. 7 shows a cross sectional view of the hypocycloid EoC mechanism in its unblocked position through the line A-A of FIG. 2.
Figure 8:
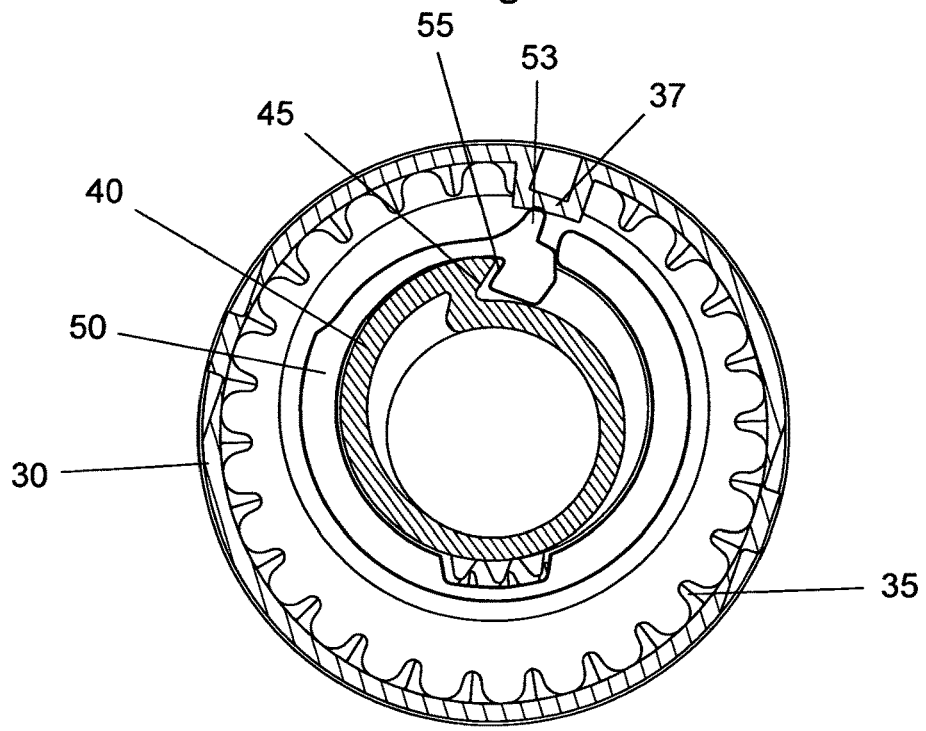
FIG. 8 shows a cross sectional view of the hypocycloid EoC mechanism in its blocked position through the line B-B of FIG. 2.

The principle of the hypocycloid geared EoC mechanism is shown in FIGS. 6 to 8. The internal surface 36 with the internal diameter (D) of the drive tube 30 supports the external surface 56 with the external diameter (d) of the EoC ring 50. Whenever the drive tube 30 is rotated around its centre axis X, e.g. in the counter-clockwise direction as indicated by the arrow A in FIGS. 6 and 7, the EoC ring 50 rotate around its centre axis Y in the same direction (indicated by the arrow B in FIG. 6-7). When the drive tube 30 is rotated one full revolution (=360 degrees), the EoC ring 50 rotates an angle greater than one full revolution (>360 degrees) due to hypocycloid gearing. The angle that the EoC ring 50 rotates depends on the diameter ratio between the internal diameter (D) of the drive tube 30 and the external diameter (d) of the EoC ring 50. This is referred to as the modulus for the hypocycloid gearing and is expressed as; m=D/d.

In the example in FIG. 6, the diameter ratio, the modulus, is 2 i.e. the internal diameter (D) is twice the external diameter (d). As a result the EoC ring 50 will rotate 720 degrees around its own centre axis Y whenever the tube 30 is rotated 360 degrees around its centre axis X. Mathematically, the circumference of the internal surface 36 of the tube 30 in the example is the double of the circumference of the external surface 56 of the EoC ring 50 ($C_D$=π×D Vs. $C_d$=π×d), thus the EoC ring 50 rotates two full revolutions every time the tube 30 rotate one revolution. In FIG. 7, the outer diameter (d) of the EoC ring 50 is the top of the teeth 51 and the inner diameter (D) of the drive tube 30 is the bottom of the valleys 34.

The example disclosed in FIGS. 7 and 8 is suitable for an injection containing 600 I.U of insulin e.g. provided as 3 ml of insulin having a strength of 200 I.U per ml. If e.g. the dose setting is configured for 24 I.U of insulin per full revolution, the dose setting mechanism needs to be able to rotate (600/24=) 25 Full revolutions before all 600 I.U has been set where after further rotation most be prevented. The stopping mechanism will be explained later, but implicates in one example that one of the valleys 34 between the last two teeth 35 are filled out as explained below.

In the example of FIG. 7, the single tooth 53 carried by the flexible arm 52 were initial located in the first valley 34a of the drive tube 30. The last two teeth 35 (last when moved counter-clockwise, in the direction of arrow A) are joined together with no valley separating the two teeth 35, thereby forming one double tooth 37. As a result there are 25 usable valleys 34 as the $26^{th}$ valley is blocked out. Since the single tooth 53 initially is positioned in the first valley 34a it can move through the following 24 valleys 34 and into the blocked out valley of the double tooth 37, all together a movement of (24+1) 25 steps. In FIG. 7, the teeth 53 are located in the $25^{th}$ valley.

The angular distance between each valley 34 is (360/26): 13.85 degrees as there are 25 steps (usable valleys 34) plus the missing valley of the double tooth 37, all together 26 steps (valleys).

The single tooth 53 carried by the flexible arm 52 therefore has to move (360+360/26) 373.85 degree for each full revolution (360 degree) of the drive tube 30. This is done by having a gearing modulus of (373.85/360)=1.0385.

The effect of this gearing is that for each full revolution (360 degrees) of the drive tube 30 the EoC ring 50 rotates 373.85 degrees in the same rotational direction and the single tooth 53 is delivered into the next consecutive valley 34b. This can be done 25 times before the single tooth 53 reaches the 26th blocked out valley of the double tooth 37.

In FIG. 7, the single tooth 53 has been moved through 23 valleys and is now positioned in the $25^{th}$ and last accessible valley 34c (it started in the first valley). When the drive tube 30 is rotated one more full rotation of 360 degrees, the EoC ring 50 will rotate 373.85 degrees and the single tooth 53 will be positioned in (or rather above) the blocked out valley of the double tooth 37. This is disclosed in FIG. 8.

The EoC ring 50 is provided with a suitable number of externally pointing teeth 51 in order for the EoC ring 50 to be properly rotated by the drive tube 30. In the example in FIG. 7, the EoC ring 50 carries 24 such teeth 51. As can be seen best from FIG. 5A-5B one tooth has been removed adjacent to the single tooth 53 to make room for the bending of the flexible arm 52, otherwise 25 teeth 53 would be provided on the EoC ring 50.

As can be best seen from FIG. 3B, the double tooth 37 is only partly filled out (in a longitudinal direction) as only the part of the valley 34 to be engaged by the single tooth 53 needs to be filled out in order to lift the flexible arm 52 properly.

As disclosed in FIG. 8, after the EoC ring 50 has been rotated 25 full rotations, the single tooth 53 reaches the blocked out valley of the double tooth 37 and the engagement between the single tooth 53 and the double tooth 37 forces the flexible arm 52 inwardly towards the centre line Y thus moving the hook 55 radially inwardly. In this position the hook 53 engages the cut-out 45 in the clutch 40 and is prevented from further rotation as the clutch 40 is prevented from rotation during dose setting. As the EoC ring 50 is prevented from rotation so is the drive tube 30 and thus the dose setting button 10.

As the drive tube 30 has 26 valleys (and teeth) and the EoC ring has 25 teeth, the ratio of the teeth is (26/25)=1.04. Since the number of teeth, so to speak, predominates the diameter, meaning that the rotation of the EoE ring 50 is given more by the teeth ratio than the diameter (angular) ratio, this discrepancy in the tooth ratio (1.04) and the angular ratio (1.0385) actually make the EoC ring 50 rotate a little more than the mathematically required 373.85 degree. The actual rotation is (360×1.04)=374, 4 degrees, which is 0.55 degrees to many per revolution. As there is 25 revolutions, the EoC ring moves (25×0.55)=13.75 degrees to much which again equals one extra valley. The result being that the EoC ring 50 is stopped to early. However, this can be resolved by providing an extra valley, such that the drive tube 30 has 27 valleys (=26 steps).

The hypocycloid EoC mechanism of the first embodiment works as follows;

When setting a dose (FIG. 2) the clutch 40 (third element in this embodiment) is kept inrotatable and the drive tube 30 (first element in this embodiment) is rotated around its centre axis X. This rotation rotates the EoC ring 50 around its own centre axis Y. For each full revolution of the drive tube 30 the EoC ring 50 is rotated 373.85 degrees thus moving the single tooth 53 to the next consecutive valley 34b (the single tooth 53 is assumed to initially start in the first valley 34a). The EoC ring 50 in this way counts one incremental step for each revolution of the dose setting member 10. As the drive tube 30 is provided with 24 accessible steps or valleys 34 (one of the altogether 26 valleys is blocked out and one is the starting position) and one double tooth 37, 25 incremental steps or 600 I.U are available when counting 24 I.U. per full revolution of the drive tube 30. However, if less than a full revolution is turned, the EoC ring 50 will still remain in this position.

When the set dose is expelled, the clutch 40, the drive tube 30 and the EoC ring 50 rotates together such that the relative position between the three parts (40, 30, 50) are maintained. The angular position of the single tooth 53 inside the drive tube 30 at any given time is thus an expression of the accumulated number of set doses. The doses set in previous dose settings has of course been expelled, the counting is thus the already set and expelled doses+the latest setting.

When the drive tube 30 has been rotated 25 full rotations, the single tooth 53 encounters the double tooth 37 of the drive tube 30 and the single tooth 53, the flexible arm 52 and the hook 55 are lifted radially inwards. In this inwardly bended position, the hook 55 will engage with the cut-out 45 in the clutch 40 during the rotation. Since the clutch 40 is kept inrotatable during dose setting, the engagement between the hook 55 and the cut-out 45 of the clutch 40 will prevent further rotation of the EoC ring 50 and thereby also prevent further rotation of the drive tube 30, thus preventing further dose setting.

Leading up to the cut-out 45 a ramp 46 is provided such that when the hook 55 on the last part of the last rotation encounters the double tooth 37 sufficient space is provided to begin the radially inwards movement of the hook 55. Since both the drive tube 30 and the EoC element 50 rotate together, however with the EoC ring 50 moving a little faster, the abutment between the single tooth 53 and the double tooth 37 will happen graduately on the last part of the rotational movement.

The above example is for illustration only. The hypocycloid geared EoC mechanism can be made with any size of internal diameter (D) and internal diameter (d) and with any suitable number of teeth and with any suitable angular position of the teeth.

Further, as the EoC mechanism in the example is designed for a maximum of 25 full rotations it can easily be assembled with the single tooth 53 in a different initial starting position. If e.g. the single tooth 53 is pre-mounted to start in a different valley 34 (e.g. in the valley named "34d") such that the single tooth 53 only has to climb 11 valleys 34 before reaching the double tooth 37, the drive tube 30 can thus be rotated 12 full rotations. At the same time the cut-out 45 of the clutch 40 can be arranged opposite thereby further adding a half rotation to the 12 full rotations. Such design is particular suitable for an injection device containing 300 I.U. of insulin and 24 increments per full rotation (24× 12.5=300). Such an injection device could e.g. contain 3 ml of a U100 insulin.

In this manner it is possible to use only a part of the valleys 34 or to use a different modulus for the hypocycloid gearing thus designing the EoC mechanism for the relevant drug and the relevant number of strength and doses.

FIG. 9-12 discloses a second embodiment. The similar components in this embodiment are numbered with the same number as in the first embodiment plus 100. The second clutch 15 in the first embodiment which in the second embodiment is the third element is thus numbered with a "115".

In the second embodiment, the EoC mechanism has been moved to the proximal end of the injection device 1 and configured slightly different as will be explained. In the first embodiment the cam 43 is carried by the clutch 40 whereas, since the EoC mechanism has been moved proximally in the second embodiment, the cam 143 is in the second embodiment carried by the second clutch 115.

The second clutch element 115 (third element in this embodiment) is proximally provided with a ratchet arm 116 which engages a first toothing 111 in the spring base 109. The spring base 109 is retained in the housing 1 as in the first embodiment, however in this second embodiment the spring base 109 operates as the first element. The clutch 115 and the spring base 109 have a centre axis X.

The spring base 109 is further provided with a second toothing 135 which engages with the toothing 151 of the EoC ring 150. As in the first embodiment, the toothing 135 defines valleys 134 and is carried on the internal surface 136 of the spring base 109 having a diameter (D), and the toothing 151 of the EoC ring 150 defines an external surface 156 having a diameter (d).

The spring base 109 is further provided with an internal tower 112 having a longitudinal opening 113. The longitudinal opening 113 is utilized to stop the rotation of the EoC ring 150 as will be explained.

The clutch 115 is further provided with an eccentric cam 143 having a centre axis Y which is dislocated in relation to the centre axis X. As in the first embodiment, the injection button 10 engages the second clutch 115 which is rotated during dose setting.

The EoC ring 150 of the second embodiment is further disclosed in FIG. 10. Externally the EoC ring 150 is provided with a toothing 151 which engages the similar toothing 135 internally in the spring base 109. The EoC ring 150 of the second embodiment is further provided with a flexible arm 152 which carries an inwardly pointing hook 155.

As can be seen in FIG. 9, the EoC ring 150 is provided with an inwardly pointing protrusion 157 which is engaged with a non-shown track in the second clutch 115 such that the EoC ring 150 can only rotate relatively to the second clutch 115 but is hindered in axial movement.

During injection the second clutch 115 is moved axially in the proximal direction against the force of the spring arm 118. This is the same functionality as in the first embodiment where the clutch 15 is pushed proximally by a non-shown needle shield. This proximal movement is conveyed to the second clutch 15 ("115" in the second embodiment). In the dose setting mode, the spring arm 118 urges the second clutch in the distal direction.

Figure 11:
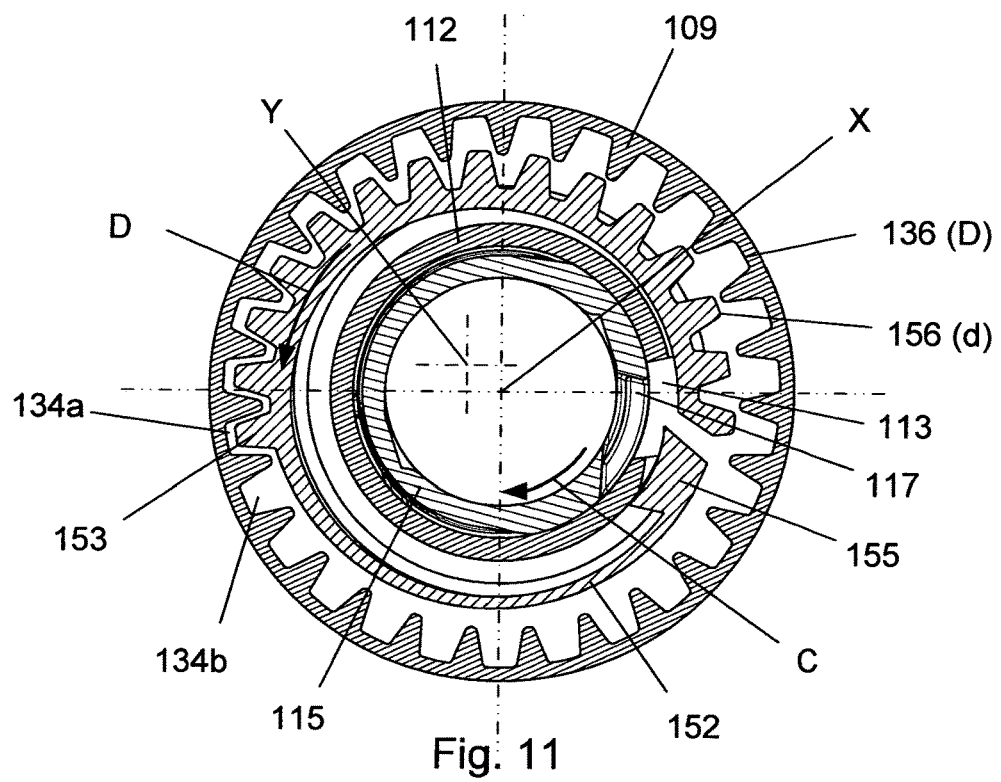
FIG. 11 show a cross sectional view of the hypocycloid EoC mechanism according to the second embodiment in its unblocked position.
Figure 12:
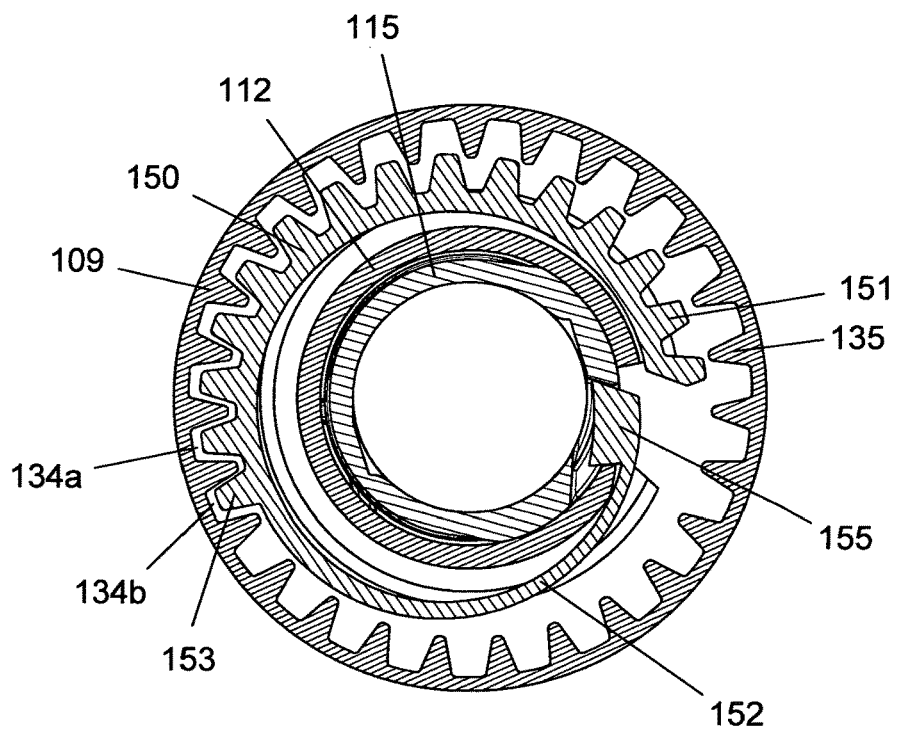
FIG. 12 show a cross sectional view of the hypocycloid EoC mechanism according to the second embodiment in its blocked position.

The hypocycloid EoC mechanism of the second embodiment works as follows; FIGS. 11 and 12 are sectional views of the EoC mechanism. The spring base 109 is secured to the housing 1 and the EoC ring 150 is in toothed engagement via the toothing 135/151 with the spring base 109. The EoC ring 150 has a smaller diameter (d) than the diameter (D) of the spring base 109 and thus operates as the inner circle of a hypocycloid gearing.

Each time the EoC ring 150 is rotated a specific tooth 153 is moved from one prior valley 134a to the next consecutive valley 134b. However in the first embodiment the single tooth 53 was moved 373.85 degrees for each rotation of the first element (drive tube 30) as the ratio was calculated to 1.0385.

In the second embodiment however the rotating part is the second clutch 115 carrying the eccentric cam 143. The spring base 109 (first element) is inrotatable secured in the housing 1. Rotation of the second clutch 115 and the cam 143 in the clockwise direction as indicated by the arrow "C" makes the EoC ring 150 rotate in the opposite direction (counter-clockwise, indicated by the arrow "D"). Since the rotational direction is opposite 360 degrees must be deducted from the 373.85 degrees required if the rotational direction is the same as in the first embodiment. The result is that the EoC ring 150 rotates (373.85−360) 13.85 degrees (in the opposite direction) for each 360 degrees rotation of the second clutch 115.

If, in a thought and non-shown example, the spring base 109 could be the rotational part, which in FIG. 11-12 would result in the EoC ring 150 rotating 373.85 degrees for each full rotation of the spring base 109, and in the same rotational direction as in the first embodiment. The specific tooth 153 would thus be moved from the prior valley 134a through 373.85 degrees and into the end valley 134b.

In FIG. 12, the second clutch 115 has been rotated one full rotation (360 degrees) compared with FIG. 11 with the result that the specific tooth 153 have moved from the prior valley 134a to the next consecutive valley 134b. During rotation of the EoC ring 150 the hook 155 of the flexible arm 152 slides on the outside surface of the tower 112 of the spring base 109. As the EoC ring 150 rotate 13.85 degrees for each full rotation of the second clutch 115, the hook 155 eventually arrives at the longitudinal opening 113 in the tower 112 as depictured in FIG. 12. In this end position, a cut-out 117 in the second clutch 115 will align with the longitudinal opening 113 and the hook will engage both the tower 112 of the non-rotational spring base 109 and the second clutch 115 which prevents further rotation of the EoC ring 150 and of the second clutch 115.

In the second embodiment, the start position of the specific tooth 153 together with the start position of the cut-out 117 in the second clutch 115 (both positions seen in relation to the longitudinal opening 113 in the tower 112 of the spring base 109) defines the number of steps the EoC ring 150 is allowed to make before it is stopped and further relative rotation between the EoC ring 150 and the spring base 109 is prevented. As the EoC ring 150 rotate one step for each full rotation of the second clutch 115, the stop function applied between the EoC ring 150 and the spring base 109 is also conveyed to the rotational movement of the second clutch 115 which is therefore also prevented from further rotation Some preferred embodiments have been shown in the foregoing, but it should be stressed that the invention is not limited to these, but may be embodied in other ways within the subject matter defined in the following claims. It is especially stressed that the described hypocycloid geared EoC mechanism can by following the above be adjusted to accommodate any size of dosing from any initial content of liquid drug. It is further stressed that the disclosed positions of the EoC mechanism in the described embodiments could be different. The EoC mechanism could e.g. be provided in a different injection device and e.g. in a different position in the injection device.

The invention claimed is:

1. A pen-shaped injection device for delivering set doses of a liquid drug comprising:
   a torsion spring which is strained when setting a dose and released to drive a piston rod forward during dose expelling and the injection device further comprises a non-axial working End-of-Content (EoC) mechanism comprising:
   a first element having a first internal surface with a first internal diameter (D),
   an EoC element having a second external surface with a second external diameter (d) being smaller that the first internal diameter (D) and the EoC element is located inside the first internal diameter (D) of the first element,
   wherein the first element has a first centre axis (X), and the EoC element has a second centre axis (Y) not coaxial in relation to the first centre axis (X) and wherein the second external surface of the EoC element engages with the first internal surface of the first element,
   wherein the first element and the EoC element rotates relatively to each other in a gearing ratio,
   wherein stopping structure is provided for stopping the relative rotation of the first element and the EoC element in a predetermined position,
   whereby a dose size exceeding the remaining injectable content of liquid drug cannot be set,
   wherein the EoC element rotates on a cam provided on a third element during dose setting,
   wherein the third element carrying the cam is rotated to set a dose and the first element is kept inrotatable during dose setting, and
   wherein the EoC mechanism has no components operating in the axial direction when counting.

2. An injection device for delivering set doses of a liquid drug comprising
   a torsion spring which is strained when setting a dose and released to drive a piston rod forward during dose expelling and the injection device further comprises a non-axial working End-of-Content (EoC) mechanism comprising:
   a first element having a first internal surface with a first internal diameter (D),
   an EoC element having a second external surface with a second external diameter (d) being smaller that the first internal diameter (D) and the EoC element is located inside the first internal diameter (D) of the first element,
   wherein the first element has a first centre axis (X), and the EoC element has a second centre axis (Y) not coaxial in relation to the first centre axis (X) and wherein the second external surface of the EoC element engages with the first internal surface of the first element,
   wherein the first element and the EoC element rotates relatively to each other in a gearing ratio,
   wherein stopping structure is provided for stopping the relative rotation of the first element and the EoC element in a predetermined position,
   whereby a dose size exceeding the remaining injectable content of liquid drug cannot be set,
   wherein the EoC element rotates on a cam provided on a third element during dose setting,
   wherein the third element carrying the cam is rotated to set a dose and the first element is kept inrotatable during dose setting, and
   wherein the EoC mechanism has no components operating in the axial direction when counting.

* * * * *